United States Patent [19]

von Castelmur

[11] 3,938,531

[45] Feb. 17, 1976

[54] SMOKING MATERIAL AND THE PROCESS OF MAKING THE SAME

[75] Inventor: Hans von Castelmur, Basel, Switzerland

[73] Assignee: Tamag Basel AG., Basel, Switzerland

[22] Filed: Dec. 17, 1973

[21] Appl. No.: 425,115

[30] Foreign Application Priority Data

Dec. 28, 1972 Luxemburg............................ 66773
Feb. 14, 1973 Luxemburg............................ 67028

[52] U.S. Cl................. 131/17 A; 131/2; 131/140 C
[51] Int. Cl.²................... A24B 13/00; A24B 15/08
[58] Field of Search............ 131/2, 15, 17, 140–144, 131/264–269, 140 C; 260/96.5, 553 A; 208/25

[56] References Cited
UNITED STATES PATENTS

| 3,025,860 | 3/1962 | Grossenbeck et al. | 131/140 C |
| 3,085,581 | 4/1961 | Rosenberg | 131/144 |
| 3,125,098 | 3/1964 | Osborne | 131/140 C |
| 3,288,146 | 11/1966 | Bavley et al. | 131/17 R |
| 3,654,934 | 4/1972 | Martin | 131/267 |
| 3,729,009 | 4/1973 | Stevens et al. | 131/2 |

OTHER PUBLICATIONS

"Crystalline Adducts of Urea With Linear Aliphatic Compounds", paper by Zimmerschied et al., presented at Joint Symposium on Adsorption–The Division of Petroleum Chemistry –Atlantic City, Sept 1949, pp. 225–229 cited.

Primary Examiner—Robert W. Michell
Assistant Examiner—V. Millin
Attorney, Agent, or Firm—Karl F. Ross; Herbert Dubno

[57] ABSTRACT

A smoking material and the process of making the material so that the material serves as a smoke-producing substitute for smoking tobacco, regenerated tobacco, or the like, wherein the material is molded from a homogeneous aqueous mash of comminuted botanicals, binders and plasticizers with addition of nitrogen donors and flavoring compounds. The preferred additives are urea compounds of vanillin or paraffin being from the group consisting of vanillylidene-urea $C_9H_{10}N_2O_3$ and divanillylidene - urea $C_{17}H_{16}N_2O_3$.

5 Claims, No Drawings

SMOKING MATERIAL AND THE PROCESS OF MAKING THE SAME

The invention relates to a process for making a material serving as a smoke-producing composition for aromatic candles, smoking-tobacco substitutes and regenerates, and the like, by molding said material from a homogeneous aqueous mash with the addition of flavoring compounds. The invention also relates to the composition as thus made.

When tobacco substitutes are made for smoking, the mash contains parts of plants other than tobacco (comminuted botanicals), some chemicals, (e.g. binders and plasticizers), and sometimes also natural tobacco. By adding flavoring substances to the mash, acrid components of the smoke, which are caused by the presence of the plants other than tobacco, can be suppressed or limited in their effect upon the "taste". The known flavoring ingredients are vanillin and paraffin, which suppress the acrid component causing the rough taste, and leave a pleasant taste and aroma when smoking, and a satisfactory aroma in the air when burning a candle.

However, the addition of vanillin and/or paraffin to the aqueous mash can be disadvantageous. Thus, vanillin added to the smoke-producing material, or to the mash, has the undesirable property of sublimating out of the finished material in the shape of small white crystalline needles. Furthermore, because of its high vapor pressure, vanillin emits an intense unpleasant odor even under normal conditions, that is to say in the cold and while the material is not burning. If, on the other hand, the addition of vanillin to the mash is decreased to an extent that the odor and crystal formation are suppressed, the improvement in the taste when smoking is lost.

The addition of paraffin to the substitute material or to the mash has the inconvenience that in its pure state it is insoluble in water which prevents it from being uniformly distributed in the mash. Local concentrations may occur except where there is a quantity of paraffin below that required for the desired effect. At regions of local excess, an unpleasant greasy odor is emitted even when the composition is cold and is noticeable also during burning.

It is an object of the present invention to provide a process for making an improved smoke-generating composition which will overcome the drawbacks of the known processes.

It is a further object of the invention to provide a process for making a composition for aromatic candles, smoking tobacco, and regenerated tobacco, which, in the finished state will emit a pleasant odor when burned, and which will be free from any acrid flavor when smoked.

In accordance with the invention the above objects are achieved by adding to an aqueous homogeneous mash of the substances from which the finished products are to be obtained, the flavoring ingredient in the form of a urea compound. It has been found that in so proceeding it is possible to maintain the improved flavor, taste and aroma of the composition, while avoiding the shortcomings mentioned above. It is of particular advantage that the urea forming part of the flavoring compound, is an excellent nitrogen donor, the use of which provides nitrogen content corresponding to that of natural tobacco, a fact which is especially desirable where tobacco substitutes and regenerates are concerned, since a certain amount of nitrogen is desirable for a pleasant smoke.

The vanillin urea compounds to be used are vanillylidene urea and divanillylidene urea. These two compounds have a considerably lower vapor pressure than vanillin so that under normal conditions and with the concentrations here concerned, no undesirable vanillin odor will be noticed. This applies especially to divanillylidene urea which has a lower vapor pressure than vanillylidene urea and is therefore the preferred compound. It is also preferred because its vanillin content is higher than that of vanillylidene urea so that a smaller quantity thereof will serve the desired purpose.

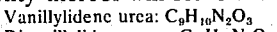
Vanillylidene urea: $C_9H_{10}N_2O_3$
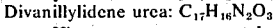
Divanillylidene urea: $C_{17}H_{16}N_2O_3$ The paraffin urea compound which can be used according to the invention is an addition compound which, unlike paraffin, is soluble in water and which does not emit an undesirable odor under normal condition. In paraffin urea, several urea molecules are added to each paraffin molecule so that the compound may be illustrated by the following formula

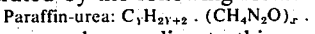
Paraffin-urea: $C_yH_{2y+2} \cdot (CH_4N_2O)_x$.

A compound according to this empirical formula with $y=10$ and $x=8$, and another compound with $y=4$ and $x=4$, are preferred for the use of the present invention. In the addition compound with the values $y=10$ and $x=8$, the paraffin-urea molecules are formed from a paraffin molecule with 10 carbon atoms to which eight urea molecules are added. It was found that, in accordance with the invention, vanillin urea can be added in an amount calculated on the dry mash of 0.03 to 1% by weight vanillin, while the values for paraffin urea are 0.3–4% by weight paraffin; in both cases, no unpleasant odor component will be present in the finished substitute material. No annoying odor is noticed even when the mash has added thereto not only a dry amount of vanillin urea, ranging from 0.03 to 1% by weight vanillin, but also at the same time a dry amount of paraffin urea ranging from 0.3 to 4% by weight paraffin. It has further been found that with the mentioned concentrations, even with unfavorable conditions, acrid taste components in the smoke such as may be caused, for instance by burning cellulose, will be cut down to a significant extent.

When smoking or burning of the substitute material occurs, the added urea compound is decomposed in the incandescent zone. At that time, nitrogen is liberated from the urea component, which likewise acts to improve the flavor of the smoke.

The aqueous mash, in accordance with the present invention, preferably consists of 40 to 60% by weight of the dry ingredients comminuted botanicals, most advantageously cereal-grain wastes or chaff, not shells and tobacco wastes; 12 to 28% by weight of the dry ingredients of inorganic and organic compounds and fillers, especially magnesium formate, tartaric acid, potassium nitrate, ammonium phosphate and calcium carbonate; 6 to 16% by weight of the dry ingredients of binders such as cellulose or dellulosic compounds and pectin; 7 to 21% by weight of the dry ingredients of plasticizers, especially ethylene glycol and glycerol; 5 to 15% by weight of the dry ingredients of flavorings such as fruit concentrates and caramel. As indicated, vanillin and paraffin are added as the urea addition compounds in the stated amounts.

EXAMPLE 1 a. Substitute for Smoking Tobacco

2000 Grams of wheat bran, 2000 grams of oat chaff, and 500 grams of cacaonut shells were ground in dry state and suspended to make a paste in 30 liters of water. The paste is ground in wet state at a temperature of between 45° and 55°C. 600 Grams of magnesium formate, 150 grams of tartaric acid, 300 grams of potassium nitrate, 300 grams of diammonium-hydrogen phosphate and 50 grams divanillylidene urea (obtained as described below) are stirred in the form of a powder into 30 liters of water, until all have been dissolved. To that solution, 600 grams of calcium carbonate, 1125 grams of NaCMC (sodiumcarboxymethyl cellulose) and 50 grams of pectin are added with vigorous stirring. The solution is stirred vigorously for about 5 minutes and is then allowed to stand for 30 minutes, while being briefly stirred every 5 minutes. Subsequently, 75 grams of glyoxal of 40% are poured into the solution.

Into the so obtained solution, the above described paste is stirred and a mash is formed, into which are stirred 1350 grams glycerol, 150 grams of diethylene glycol, 1000 grams of concentrate of fruits, and 100 grams of caramel.

The mash is spread on an endless conveyor and made into a strong tobacco foil by drying; the foil has a vanillin content of about 0.5% dry weight, but does not display any noticeable vanillin odor nor can crystal formation be observed.

b. Preparation of Divanillylidene urea

3000 Grams of vanillin and 600 grams of urea, corresponding to about 2:1 in the molar ratio, are pulverized and mixed, and are heated with constant vigorous stirring to 115°C. The heating occurs at a rate of 10°C in 5 minutes. Obtained is a yellow-brown melt of divanillylidene urea, which is cooled and powdered. The so obtained powder of divanillidylidene urea is also used in Example 5.

EXAMPLE 2

Substitute for Smoking Tobacco

The procedure is the same as described in Example 1, with the only difference that 60 grams of vanillylidene urea are stirred in instead of 50 grams of divanillylidene urea. The vanillin content of the so produced tobacco substitute foil is likewise about 0.5% of dry weight. No vanillin odor or crystal formation are present in the finished substitute tobacco foil.

EXAMPLE 3

Substitute for Smoking Tobacco

The procedure is the same as in Example 1a, with the only difference that 1000 grams paraffin urea of the empirical formula $C_{10}H_{22} \cdot (CH_4N_2O)_8$ are used instead of 50 grams divanillylidene urea. The paraffin content of the substitute tobacco foil obtained is about 2% of dry weight. No paraffin odor is noticeable in the finished foil.

EXAMPLE 4

Substitute for Smoking Tobacco

The procedure is the same as in Example 1a, with the only difference that instead of 50 grams divanillylidene urea, 15 grams of vanillylidene urea and 1500 grams of paraffin urea of the formula $C_{10}H_{22} \cdot (CH_4N_2O)_8$ are used. The vanillin content of the so obtained tobacco substitute foil is 0.1% of dry weight and the paraffin content 3% dry weight. Neither vanillin odor nor crystal formation are noticeable in the finished product, nor is a paraffin odor present.

EXAMPLE 5

Smoking Tobacco Regenerate

The procedure is the same as in Example 1, with the only difference that instead of 5000 grams chaff and shells, 5000 grams natural tobacco wastes, as obtained from the manufacture of cigarettes, are suspended. The molded regenerate foil has a vanillin content of about 0.5% dry weight. No vanillin odor and crystal formation noticeable in the finished regenerate foil.

EXAMPLE 6

Smoking Tobacco Regenerate

The procedure is the same as in Example 5, with the only difference that instead of 50 grams of divanillylidene urea, 8 grams of vanillylidene urea were added. The molded tobacco regenerate foil has in that case a vanillin content of about 0.06%/dry weight. No vanillin odor or crystal formation was observed in the finished foil.

EXAMPLE 7

Smoking Tobacco Regenerate

The procedure is the same as in Example 5, with the only difference that instead of 50 gram of divanillylidene urea, 150 grams of paraffin urea of the formula $C_4H_{10} \cdot (CH_4N_2O)_4$ were added. The molded tobacco regenerate foil has a paraffin content of about 0.3% dry weight. No paraffin odor is noticeable in the finished regenerate foil.

EXAMPLE 8

Incense Candle

The composition as produced in Example 1 was made, except with three times the amount of potassium nitrate, and was formed into a conical candle and provided with a central wick. Neither a vanillin odor nor crystals of vanillin are found with the product which burns slowly with a pleasant odor.

EXAMPLE 9

Production of Divanillylidene urea

3000 Grams of vanillin and 600 grams of urea, corresponding to a molar ratio of about 2:1, are pulverized, mixed, and heated to 115°C with constant vigorous stirring. The heating occurs at a rate of 10°C in 5 minutes. Obtained is a yellow-brown melt of divanillylidene urea which is cooled and pulverized. The so obtained divanillylidene urea in powder form is used as described in Examples 1a and 5.

The substance to be smoked or burned made in any of the examples will yield a smoke of pleasantly mild and aromatic odor.

I claim:

1. A smoke-generating material, especially as synthetic or regenerated tobacco, which consists essentially of: 40 to 60% by weight of comminuted botanicals in the form of cereal-grain, nut, and tobbaco scraps and waste;

12 to 28% by weight of inorganic and organic fillers and compounds selected from the group which consists of magnesium formate, tartaric acid, potassium nitrate, ammonium phosphate and calcium carbonate;

6 to 16% by weight of cellulosic substances and pectin binders;

7 to 21% by weight of ethylene glycol and glycerol as plasticizers;

5 to 15% by weight of flavorings; and 0.03 to 1% by weight of a vanillin compound of urea selected from the group consisting of vanillylidene-urea $C_9H_{10}N_2O_3$ and divanillylidene-urea $C_{17}H_{16}N_2O_3$.

2. The smoke-generating material defined in claim 1 further consisting of 0.3 to 4% by weight of a paraffin compound of urea.

3. In the production of a smoke-generating material in which an aqueous mash consisting essentially of comminuted botanicals, binders, fillers and plasticizers is molded and dried to form the material, the improvement which comprises adding to said mash a flavor-enhancer in the form of a definite vanillin-urea compound formed by melting vanillin and urea together, said compound decomposing upon burning of said material and being from the group consisting of vanillylidene-urea $C_9H_{10}N_2O_3$ and divanillylidene-urea $C_{17}H_{16}N_2O_3$ compound being added in an amount corresponding to 0.03 to 1% vanillin of the dry ingredients of the mash.

4. The improvement defined in claim 3 wherein said compound is divanillylidene-urea $C_{17}H_{16}N_2O_3$.

5. The improvement defined in claim 3 wherein the flavor-enhancer includes 0.3 to 4% by weight of a paraffin compound of urea.

* * * * *